US00PP15208P2

(12) United States Plant Patent
McNaughton

(10) Patent No.: US PP15,208 P2
(45) Date of Patent: Oct. 5, 2004

(54) ***LAVANDULA* PLANT NAMED 'LAVSTS 08'**

(50) Latin Name: *Lavandula stoechas*
Varietal Denomination: Lavsts 08

(76) Inventor: Virginia McNaughton, Lavender Downs, Lawford Road, West Melton, RD6 Christchurch (NZ)

( * ) Notice: Subject to any disclaimer, the term of this patent is extended or adjusted under 35 U.S.C. 154(b) by 0 days.

(21) Appl. No.: 10/663,848

(22) Filed: Sep. 15, 2003

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—S B McCormick-Ewoldt

(57) ABSTRACT

A new cultivar of *Lavandula* plant named 'Lavsts 08' that is characterized by burgundy-purple sterile bracts and low, compact bushy habit. These traits set it apart from all other existing varieties of *Lavandula* known to the inventor.

2 Drawing Sheets

Genus: *Lavandula.*
Species: *stoechas.*
Denomination: Lavsts 08.

BACKGROUND OF THE INVENTION

The present invention relates to a new and distinct cultivar of lavender known botanically as *Lavandula stoechas* subsp. *pedunculata* and hereinafter referred to by the cultivar name 'Lavsts 08'. The new invention is a product of pollination between two *Lavandula stoechas* varieties and was discovered in a cultivated area of Canterbury, New Zealand by the inventor in 1997. Because of its hybrid nature, it will be known as *Lavandula* 'Lavsts 08'. The female parent plant is an unidentified cultivar of *Lavandula stoechas* (unpatented) and the male parent plant is an unidentified cultivar of *Lavandula stoechas* (unpatented).

The new Lavender plant 'Lavsts 08' was selected for its distinct and unique low compact growth habit, spike colour, and sterile bract colour. 'Lavsts 08' is distinguishable from the parent plants by size of the plant and color of the sterile bracts. There are no comparison plants known to the inventor.

'Lavsts 08' was asexually propagated by the inventor in Christchurch, New Zealand in 1998 using soft to semi-hardwood cuttings. Since that time subsequent generations have been determined fixed, stable and true to type.

SUMMARY OF THE INVENTION

The following traits have been repeatedly observed and represent the distinguishing characteristics of the new lavender cultivar 'Lavsts 08'. These traits in combination distinguish 'Lavsts 08' from all other existing varieties of *Lavandula* known to the inventor. 'Lavsts 08' has not been tested under all possible conditions and phenotypic differences may be observed with variations in environmental, climatic, and cultural conditions, however, without any variance in genotype.

1. *Lavandula* 'Lavsts 08' exhibits a low, compact, bushy habit.
2. *Lavandula* 'Lavsts 08' exhibits burgundy-purple sterile bracts.
3. *Lavandual* 'Lavsts 08' exhibits dark violet spikes.
4. *Lavandula* 'Lavsts 08' exhibits lush green foliage.

BRIEF DESCRIPTION OF THE DRAWINGS

The accompanying color drawings illustrate the overall appearance of the new cultivar 'Lavsts 08' showing colors as true as it is reasonably possible to obtain in colored reproductions of this type. Colors in the drawings may differ from the color values cited in the detailed botanical description, which accurately describe the actual colors of the new variety 'Lavsts 08'.

The drawing labeled as FIG. 1 is a close-up view of a block of 6-month-old plants with first flowers. The plants shown were grown outside, under light shade, in Auckland, New Zealand.

Figure 1:
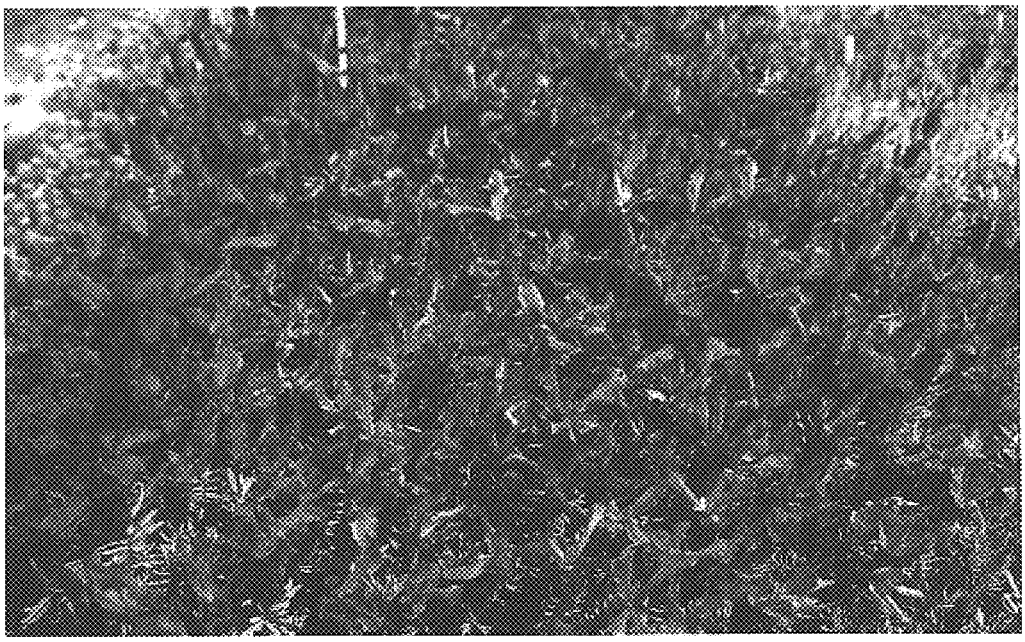
Figure 2:
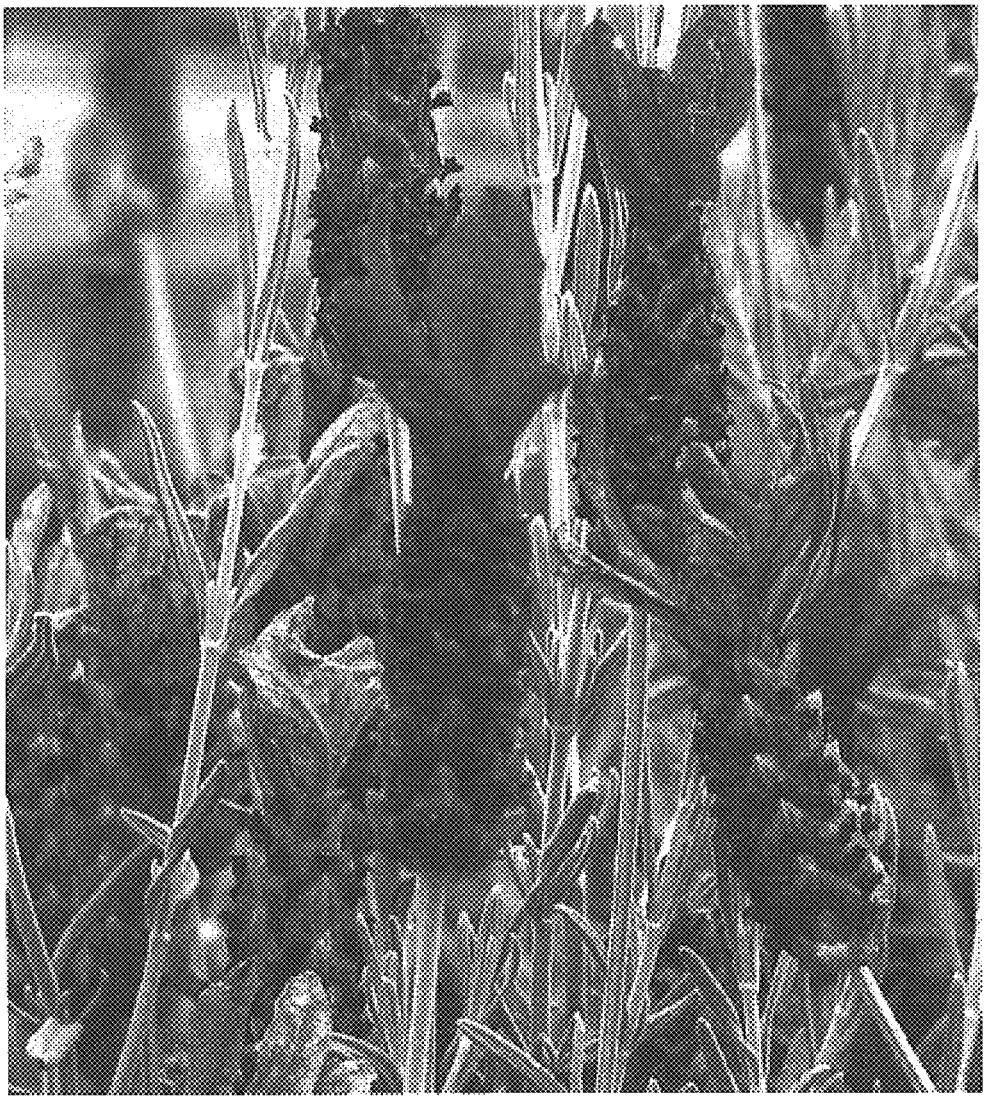

The drawing labeled as FIG. 2 is a close-up view of mature flowers on a plant, approximately 9 months old, grown outside in Encinitas, Calif.

Both drawings are made using conventional photographic techniques and although colors may appear different from actual colors due to light reflectance, they are as accurate as possible by conventional photography.

BOTANICAL DESCRIPTION OF THE PLANT

The following is a detailed description of the *Lavandula* cultivar named 'Lavsts 08'. Data was collected in West Melton, Canterbury, New Zealand from 6-month-old plants grown in the open ground and in dry conditions. Phenotypic differences may be observed with variations in environmental, climatic, and cultural conditions, without however, any difference in genotype. Color determinations are in accordance with The Royal Horticultural Society Colour Chart except where general color terms of ordinary dictionary significance are used. Color determination using The Royal Horticultural Society Colour Chart was conducted using the light box at The New Zealand Plant Variety Rights Office at Lincoln, Canterbury, New Zealand. Please note that the brown, green and violet range in these charts do not have an adequate color range to match that seen in lavender. The growing requirements are similar to the species and no disease problems have been observed.

Botanical classification: *Lavandula* 'Lavsts 08'.
Species: *stoechas.*
Common name: Lavender.

Parentage: The new hybrid 'Lavsts 08' is a product of the hybridization of the following parent plants:

*Female parent plant.*—Unidentified cultivar of *Lavandula stoechas.*

*Male parent plant.*—Unidentified cultivar of *Lavandula stoechas.*

Type: Aromatic perennial shrub.

Use: En masse, ornamental, feature, front of border or potted plant.

Growth rate: Vigorous.

Habit: Low compact bushy habit with erect, ascending flower spikes.

Shape: Rounded.

Height: 40–50 cm in height.

Spread: 40–50 cm in width.

Hardiness: USDA Zones 5–8.

Disease resistance or susceptibility: No unusual or additional disease resistance or susceptibility compared to other cultivars of the species *Lavandula stoechas.*

Propagation method: Vegetative cuttings and tissue culture.

Root system: Fibrous.

Soil: Plant in well-drained soil.

Light levels: Plant in full sun.

Special needs: Prune after flowering to maintain shape and to initiate second flowering period.

Time to initiate roots: 21 to 36 days are needed to develop roots on an unrooted cutting.

Time to develop to a one-gallon: 3 months are needed to produce a 1-gallon container plant from a rooted cutting.

Branching habit: Erect, upright and semi-open.

Seasonal interest: Flowers April–July and August.

Stem:

*Stem shape.*—Square.

*Stem surface* (*upper and lower surfaces*).—Finely puberulent.

*Stem color* (*young wood*).—165A (greyed-orange) to 199A (grey-brown).

*Stem color* (*older wood*).—165B (orange brown).

*Stem size.*—1.5 mm–5 mm in diameter.

Foliage:

*Arrangement.*—Upright stems with whorls of leaves, arranged opposite along stem. A basal pair of leaves subtend each whorl of leaves. Dense arrangement of leaves along stems.

*Leaf division.*—Simple.

*Apices.*—Acute.

*Base.*—Truncate or attenuate.

*Margins.*—Entire and revolute.

*Leaf shape.*—Linear.

*Color of mature leaves* (*upper surface*).—143A (lush green).

*Color of mature leaves* (*lower surface*).—143A (lush green).

*Color of young leaves* (*upper surface*).—143C (slightly brighter green).

*Color of young leaves* (*lower surfaces*).—Too revolute to view.

*Upper and lower surfaces.*—Pubescent on both surfaces.

*Venation.*—Mid vein depressed on upper surface and protruding beneath, side veins noticeable on lower surface.

*Internodes.*—0.3 cm–2.5 cm in length.

*Foliar fragrance.*—Heavy pine scent.

*Petiole.*—Sessile.

*Leaf length.*—Approximately 0.6 cm–3.5 cm in length.

*Leaf width.*—1 mm–3 mm in width.

Flower:

*Type of inflorescence.*—Terminal spike.

*Size of inflorescence.*—4 cm–5 cm in length and 1 cm–1.5 cm in width.

*Shape of inflorescence.*—Cylindrical with sterile bracts.

*Peduncles.*—7–8 cm in length and 10–20 mm in width.

*Peduncle color.*—145B (pale green).

*Flower shape.*—Tubular.

*Corolla.*—Two-lipped with upper lip 2-lobed and lower lip 3-lobed.

*Corolla color.*—83A (dark violet-purple).

*Calyx color.*—Pale green or pale green on lower half suffused with red-purple/burgundy on upper half. Appendage is burgundy.

*Calyx surface.*—Pubescent with tufts of longer hair at apex.

*Bracteoles.*—None present.

*Fertile bract shape.*—Cordate, rhombic-cordate or ovate and acute.

*Fertile bract color.*—Lower half membranous with green veining and outer edges red-purple/burgundy.

*Fertile bract hair covering.*—Puberulent with minute hairs along the margins.

*Sterile bract shape.*—Narrow-elliptic or oblanceolate, occasionally linear.

*Sterile bract margins.*—Strongly undulating.

*Sterile bract length.*—12–20 mm.

*Sterile bract color.*—Closest to 87A (Burgundy-purple).

*Sterile bract number.*—Five to nine.

*Fragrance.*—Heavy pine.

*Blooming period* (*New Zealand*).—October to February.

*Blooming period* (*U.S.A.*).—April to August.

Reproductive organs:

*Stamens.*—4.

*Stamen length* (*2 posterior*).—1.5 mm.

*Stamen length* (*2 anterior*).—0.5 mm.

*Pistil.*—1.

*Pistil length.*—5 mm.

*Pistil diameter.*—Less than 0.25 mm.

*Filament diameter.*—Less than 0.25 mm.

*Filament color.*—Grayish-white.

*Style length.*—4 mm.

*Style color.*—Grayish-white.

*Stigma shape.*—Oval.

*Stigma color.*—Black.

*Ovary shape.*—Globose.

*Ovary dimensions.*—Approximately 1 mm long and 0.5 mm wide.

*Ovary position.*—Superior.

*Ovary color.*—Green.

*Anther shape.*—Reniform.

*Anther length.*—Less than 0.25 mm.

*Anther color.*—Pale green.

*Pollen amount.*—Sparse.

*Pollen color.*—Orange.

Seed:

*Seed number.*—Mostly 1 per calyx; others aborted.

*Colour of seeds.*—164D (pale cream-brown).

*Length of seeds.*—1.5–2 mm. in length.

I claim:

1. A new and distinct variety of *Lavandula* plant named 'Lavsts 08' as described and illustrated.

* * * * *